United States Patent [19]

Wolfert et al.

[11] Patent Number: 4,923,745
[45] Date of Patent: May 8, 1990

[54] INSECT REPELLENT CLOTHING BAG

[75] Inventors: Barbara Wolfert, 11 Cross Ridge Rd., Chappaqua, N.Y. 10514; Ira S. Dorman, Manchester, Conn.

[73] Assignee: Barbara Wolfert, Chappaqua, N.Y.

[21] Appl. No.: 334,327

[22] Filed: Apr. 7, 1989

[51] Int. Cl.$^5$ .................. A01N 25/08; B65D 85/18
[52] U.S. Cl. .................. 428/35.4; 206/287; 206/820; 424/412; 424/416; 428/907
[58] Field of Search ............ 428/907, 35.4; 424/411, 424/412, 413, 416; 206/286, 287, 820; 223/86

[56] References Cited

U.S. PATENT DOCUMENTS

| | | | |
|---|---|---|---|
| 339,810 | 4/1886 | Regan | 424/403 |
| 663,684 | 12/1900 | Rudisch | 424/416 |
| 1,871,949 | 8/1932 | Bottrell | 514/711 |
| 2,129,659 | 9/1938 | Easling | 91/68 |
| 2,169,055 | 8/1939 | Overshiner | 167/94 |
| 3,044,885 | 7/1962 | Loehr | 424/413 |
| 3,295,246 | 1/1967 | Landsman et al. | 424/411 |
| 3,859,121 | 1/1975 | Yeadon et al. | 117/138.5 |
| 3,864,468 | 2/1975 | Hyman et al. | 424/16 |
| 3,865,235 | 2/1975 | Levy et al. | 206/286 |
| 4,008,351 | 2/1977 | Inoue et al. | 428/411 |
| 4,243,703 | 1/1981 | Palvarini et al. | 427/276 |
| 4,352,833 | 10/1982 | Young et al. | 427/4 |
| 4,576,801 | 3/1986 | Parry et al. | 427/288 |

FOREIGN PATENT DOCUMENTS

| | | | |
|---|---|---|---|
| 2284251 | 5/1976 | France | 206/286 |
| 0213703 | 12/1983 | Japan | 424/415 |

*Primary Examiner*—James Seidleck

[57] ABSTRACT

A bag article for the containment and treatment of garments and the like includes a fumigant source element within the bag, which element is activated by exposure of an internal surface to the atmosphere so as to evolve a gaseous treatment agent. The fumigant source element may be provided by a laminar pad, and activation may be achieved by parting of the panels of the bag, such as by the introduction of the garment to be contained therewithin.

19 Claims, 2 Drawing Sheets

INSECT REPELLENT CLOTHING BAG

BACKGROUND OF THE INVENTION

It is of course common practice to store clothing, blankets and other articles made of natural fibers in an atmosphere of paradicholorbenzene, for the purpose of protecting them against moths. This is usually done simply by placing the item in a relatively air-tight bag or box, and enclosing therewithin a quantity of "moth balls" or "moth flakes," which of course sublimate to evolve the protective gaseous atmosphere. Although the approach is simple and effective, the necessary materials may not always be readily at hand, and it may be inconvenient from other standpoints as well.

The prior art has recognized the desirability of providing impregnated web materials suitable for use in wrapping clothes so as to provide insect repellency. For example, Rudisch U.S. Pat. No. 663,684 describes an impregnated paper for such use, one side of which is made impermeable so as to limit escape of the active ingredient. Regan U.S. Pat. No. 339,810 is to generally similar effect.

A need remains for a garment bag, or like article, having a normally dormant fumigant source element incorporated into it, which can readily be activated to evolve a gaseous agent for treatment of the contained item, and it is the broad object of the present invention to provide a novel article having such character and capability.

A more specific object is to provide such an article in which the fumigant source element is activated simply by exposure of one of its surfaces.

Related objects of the invention are to provide a novel strip structure comprised of a multiplicity of integrally formed bags for assembling such articles, arranged end-to-end and readily seperable from one another; to provide a novel article comprised of an open-ended bag in combination with a laminar fumigant pad, providing the source element; and to provide a novel method for the containment and treatment of a garment or the like, utilizing a bag article having the foregoing features and advantages.

Additional objects of the invention are to provide such a bag article and strip structure which are relatively inexpensive and facile to manufacture, and highly convenient and effective to use.

SUMMARY OF THE INVENTION

It has now been found that certain of the foregoing and related objects of the invention are readily attained by the provision of an article comprising adjacent first and second coextensive panels of a gas barrier material, sealed about a major portion of their common peripheral margin so as to provide an open-ended bag. One of the panels of the bag is comprised of a fumigant source element on the inner face thereof, the source element being capable of evolving a gaseous agent when its inner surface is exposed. The other of the panels comprises covering means overlying and disengagably held against the inner surface of the source element, to prevent its exposure. Displacement of the covering means by separation of the panels, and consequential exposure of the source element surface, enables evolution and diffusion of the gaseous agent within the bag.

In certain embodiments the fumigant source element will be provided by a pad of laminar construction disposed between the panels of the bag. The pad will comprise a base layer affixed to one of the panels and including the fumigant source element, and a covering layer affixed to the other panel and overlying the surface of the source element. Separation of the bag panels effects displacement of the covering layer of the pad, thereby enabling evolution and diffusion of the gaseous agent.

Other objects of the invention are achieved by the provision of a strip structure providing a multiplicity of separable bag articles. It will comprise first and second coextensive webs of gaseous barrier material, usually in substantially full surface contact with one another, sealed along their lateral edges. The webs will also be sealed in a multiplicity of longitudinally spaced, transversely extending zones so as to define the bag articles thereon.

The barrier material used will normally be a film of synthetic thermoplastic resinous material, with sealing thereof being effected by fusion at an elevated temperature. In some instances however a fibrous web may desirably be employed, the material of which may be fused on one face to form a gas-impermeable skin. The panels of the bag may be provided by opposite sides of a unitary, integrally formed tubular structure, and normally they will be of substantially rectangular configuration with top, bottom and two side edges, the top and side edges being sealed so as to leave the end of the bag open along its bottom edge. In those instances in which a fumigant pad is employed, the opposite layers thereof may advantageously be fused to the panels. The covering layer will desirably be a peelable element secured to the fumigant source element with a low level of adhesion, the strength of which is substantially less than that of the bond between the pad layers and the bag panels.

Additional objects of the invention are provided by a method for the containment and treatment of a garment, or the like, wherein a fumigant pad of laminar construction is inserted into an open-ended bag, both constructed as herein above described. The opposite layers of the pad are affixed to the panels of the bag, so that separation thereof will displace the covering layer, with consequential exposure of the fumigant element surface. The action of inserting an item into the bag article will generally serve to effect parting of the panels, and resultant actuation of the pad.

DETAILED DESCRIPTION OF THE ILLUSTRATED EMBODIMENTS

Figure 1:
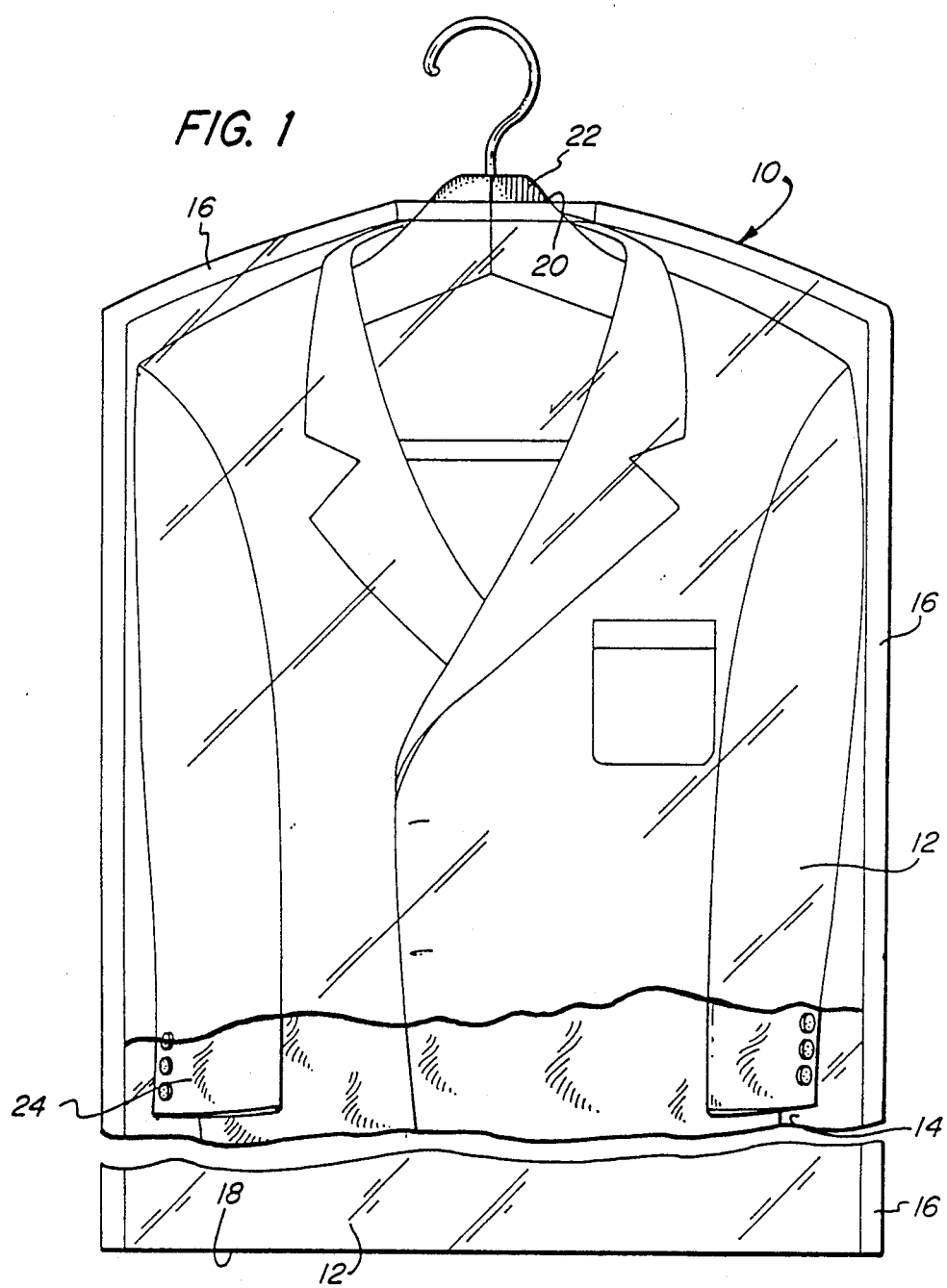
FIG. 1 is a fragmentary elevational view showing a garment on a hanger and contained within a bag article of the present invention.

Turning now in detail to FIG. 1 of the appended drawings, therein illustrated is a garment-containing bag embodying the present invention and generally designated by the numeral 10. The bag consists of coextensive panels 12, 14, which are sealed to one another by zones of heat sealing 16; it is open along the bottom edge 18, and has a relatively small disconnected section 20 at the top to permit protrusion of the hanger 22 on which the contained garment 24 is supported. Apart from the fumigant element features, which will be hereinafter described, the bag 10 may be of conventional construction.

Figure 2:
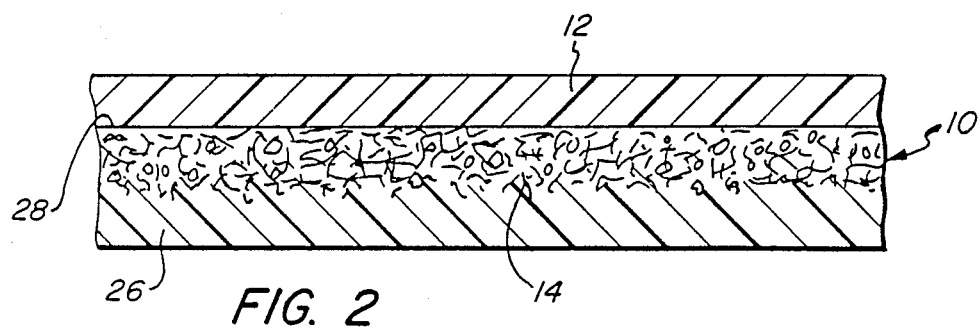
FIG. 2 is a fragmentary sectional view of a bag article embodying the invention, showing the construction of two panels of which it may be comprised.

FIG. 2 shows a section of a bag article suitable for use in providing a protective environment for a garment, in accordance with FIG. 1. Specifically, the front panel 12 of the bag 10 is provided by a sheet or film of transparent synthetic resinous material. The back panel 14 is of a composite structure produced by fusing one surface of a nonwoven fibrous web of synthetic resinous material, so as to form a gas and vapor barrier skin 26. As will be noted, the fibrous component of the panel 14 is impregnated with a solid particulate material; the impregnant has the property of evolving a gaseous agent, and may for example be paradichlorobenzene in finely divided form.

It will be self-evident that when the panels 12 and 14 are separated from one another the inside surface 28 of the back panel 14 will be exposed to the atmosphere, thereby permitting sublimation of the fumigant source material to generate paradichlorobenzene vapors. This will of course establish a protective environment for the garment 24 within the bag 10, which may advantageously be subsequently sealed at the bottom to prevent dissipation of the gas, such as by using paper-covered wire twists, or the like.

Figure 3:
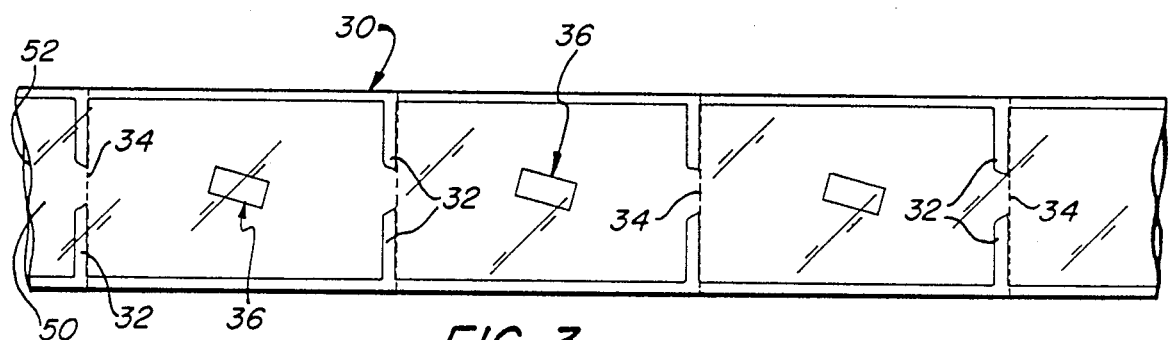
FIG. 3 is a schematic plan view illustrating a strip structure embodying the invention, and utilizing a laminar fumigant pad to provide the fumigant source element.

A multiplicity of bag articles, such as that employed in the assembly of FIG. 1, can be conveniently manufactured in the form of a continuous strip, as depicted in FIG. 3. The structure is most desirably fabricated by use of a unitary, integrally formed tube, generally designated by the numeral 30, of a synthetic resinous thermoplastic film, as may be made by a conventional blown bubble technique. The tube 30 is segmented by transversely extending zones of heat sealing, as at 32, and may be scored or lightly perforated at one end of each compartment, as at 34, so as to permit separation into individual open-ended bags. The spacing between the heat sealing zones 32 defines an area through which a hanger 22 may protrude, as indicated in FIG. 1.

Figure 4:
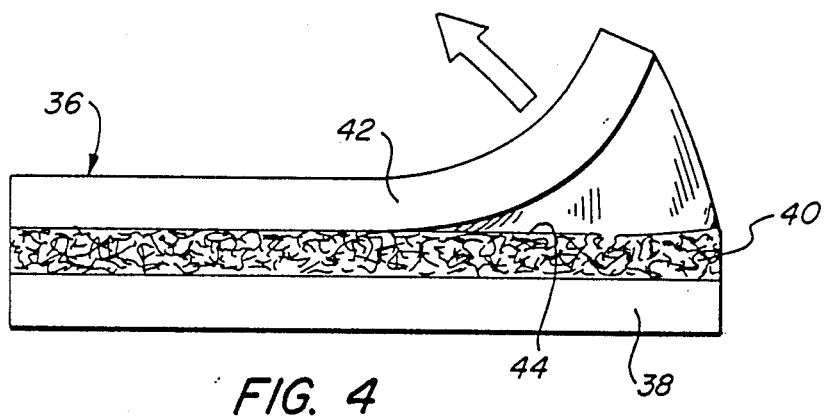
FIG. 4 is an elevational view showing a fumigant pad suitable for use herein, depicting the covering layer being peeled away from the base layer thereof.

Each compartment of the strip structure shown in FIG. 3 has contained therewithin a laminar fumigant pad or tablet, generally designated by the numeral 36. The structure of the pad 36 is shown in detail in FIG. 4, from which it can be seen to comprise a base layer, consisting of an impermeable panel portion 38 and a particulate-impregnated, fibrous web portion 40 integral therewith, providing the fumigant source element. A covering layer 42 is disposed over the surface 44 of the fibrous web portion 40, and it is lightly bonded thereto (such as by use of a suitable adhesive, not illustrated); the covering layer 42 is readily removable from the base layer to expose the surface 44, thereby permitting gasification of the active ingredient incorporated into the fumigant source element.

Figure 5:
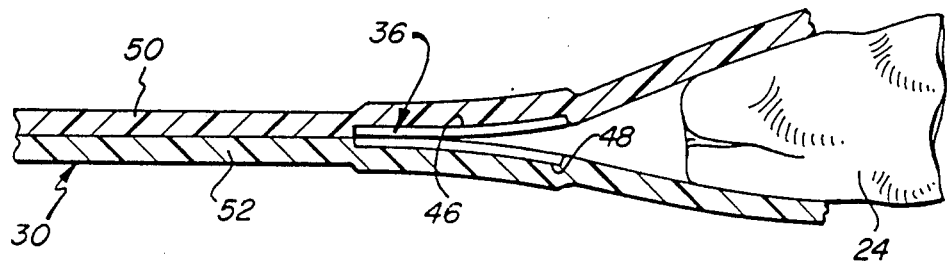
FIG. 5 is a sectional view showing a garment being introduced into a bag article of the invention, the garment serving to part the panels and thereby to actuate the fumigant pad affixed therebetween.

It will be appreciated that in fabricating the strip structure of FIG. 3 the pad 36 is interposed between the webs portions 50, 52 of which the tube 30 is comprised, and bonding thereof to the opposed surfaces 46, 48 of the fumigant tablet 36 is effected. As noted above, the level of adhesion thereby produced will be substantially greater than that which holds the covering layer 42 upon the surface 44, so that removal of the layer 42 may inherently occur upon insertion of the garment 24. FIG. 5 indicates that the mere weight of the garment will part the web panels 50, 52, in turn effecting displacement of the covering layer 42.

The panels of the bag employed in the article of the invention may or may not be of the same construction; this will be appreciated by reference to FIG. 2, on the one hand, and FIGS. 3 and 5 on the other. It might be pointed out that both panels may comprise fumigant source elements, and mutual covering members for one another.

It should also be appreciated that instead of having its own covering layer, the fumigant pad may consist of only a member having a construction that is comparable to that of the base layer described. In that case, the overlying panel portion of the bag would itself contact the fumigant source element surface, preventing its exposure until displaced.

Films of polypropylene or polyethylene will often prove most advantageous in providing a satisfactory and low-cost vapor barrier, but other plastics can of course also be employed. The carrier for the fumigant source material will advantageously be of a fibrous woven or non-woven character, made from either a natural or synthetic material; webs of rayon, nylon, polyester, polyacrylic and polypropylene fibers may be suitable, as may mats of natural fibers, such as hemp and cotton. As alternatives to utilizing a fibrous web of a thermoplastic material having an integrally formed barrier layer thereon, a separate barrier film may be laminated to a fabric layer, or a web (e.g., paper) may be coated or impregnated with a material capable of providing the necessary barrier properties; an open-cell, foamed synthetic resinous sheet may also be a suitable carrier for the impregnating agent.

The composition of the substance utilized to evolve the gaseous treatment agent may vary widely, and the choice thereof will be evident to those skilled in the art, in view of the foregoing description. As alternatives to paradichlorobenzene, the following insecticidal substances, which may be used by themselves or in combination with one another or with other insecticidal substances, may be suitable: chlorinated hydrocarbons such as lindane or methoxychlor; phosphoric acid esters such as chlorpyrifos, chlorpyrifos-methyl or dichlorvos; and pyrethroids such as vaporthrin (emphenthrin), permethrin, bioresmethrin, bioallethrin, kadethrin, decis, cyflythrin or fenfluthrin.

Although in most instances an agent having insecticidal properties will be employed, it will be appreciated that treatment with other substances in an article of the kind herein described may also be desirable, such as to impart a desired aroma to the contained item. The fumigant source substance may be solid or liquid, as long as it will readily evolve to a gaseous agent when the surface of the carrier element is exposed; heating may be relied upon to promote evaporation or sublimation, as the case may be, if so desired. Means known to those skilled in the art may also be employed to promote physical retention of the dormant fumigant substance by the carrier element.

Thus, it can be seen that the present invention provides a novel article having a normally dormant fumigant source element incorporated into it, which can readily be activated by exposure of one of its surfaces to evolve a gaseous agent for the treatment of the contained item. The invention also provides a novel strip structure comprised of a multiplicity of integrally formed bags for producing such articles, arranged end-to-end and readily separable from one another; it provides a novel article comprised of an open-ended bag in combination with a laminar fumigant pad, providing the source element; and it also provides a novel method for the containment and treatment of a garment, or the like, utilizing a bag article having the foregoing features and advantages. The structures of the invention are relatively inexpensive and facile to manufacture, and they are highly convenient and effective to use.

Having thus described the invention, what is claimed is:

1. An article for the containment and treatment of a garment or the like, comprising adjacent first and second coextensive panels of a gas barrier material sealed about a major portion of their common peripheral margin to provide an open-ended bag, one of said panels comprising, on the inner face thereof, a fumigant source element having an inner surface and capable of evolving a gaseous agent when said inner surface is exposed, the other of said panels comprising covering means overlying and disengageably held against said inner surface of said source element to prevent exposure thereof, displacement of said covering means by separation of said panels, and consequential exposure of said inner surface, enabling evolution and diffusion of said gaseous agent within said bag.

2. The article of claim 1, wherein said barrier material is a film of synthetic thermoplastic resinous material.

3. The article of claim 2, wherein said portion of said margin is sealed by fusion of said material.

4. The article of claim 2, wherein said panels are provided by opposite sides of a unitary, integrally formed tubular structure.

5. The article of claim 1, wherein said panels are in full surface contact with one another and are of substantially rectangular configuration with top, bottom and two side edges, said major portion of said margin being limited to said top and side edges of said panels.

6. An article for the containment and treatment of a garment or the like, comprising adjacent first and second coextensive panels of a gas barrier material sealed about a major portion of their common peripheral margin to provide an open-ended bag, and a fumigant pad of laminar construction disposed between said panels, said pad comprising a base layer affixed to one of said panels and including a fumigant source element having a surface remote from said one panel and capable of evolving a gaseous agent when said remote surface is exposed, and a covering layer affixed to the other of said panels and overlying and disengagably held against said remote surface of said source element to prevent exposure thereof, displacement of said covering layer, by separation of said panels, and consequential exposure of said remote surface enabling evolution and diffusion of said gaseous agent within said bag.

7. The article of claim 6, wherein said barrier material is a film of synthetic thermoplastic resinous material.

8. The article of claim 7, wherein said portion of said margin is sealed by fusion of said material.

9. The article of claim 7, wherein said panels are provided by opposite sides of a unitary, integrally formed tubular structure.

10. The article of claim 7, wherein said base and covering layers of said pad are fused to said panels.

11. The article of claim 10, wherein said covering layer is a peelable element secured to said remote surface of said source element, the level of adhesion therebetween being relatively low and substantially weaker than the adhesion of said layers to said bag panels.

12. An article for the containment and treatment of a garment or the like, comprising adjacent first and second coextensive panels of a gas barrier material sealed about a major portion of their common peripheral margin to provide an open-ended bag, and a fumigant pad disposed between said panels, said pad comprising a base layer affixed to one of said panels and including a fumigant source element having a surface remote from said one panel and capable of evolving a gaseous agent wherein said remote surface is exposed, the other of said panels comprising a covering layer overlying and disengageably held against said remote surface of said source element to prevent exposure thereof, displacement of said covering layer and consequential exposure of said remote surface enabling evolution and diffusion of said gaseous agent within said bag.

13. A strip structure comprising a multiplicity of seperable, end-to-end bag articles, each adapted, when separated from the others, for the containment and treatment of a garment or the like, said structure comprising first and second coextensive webs of gas barrier material in substantially full surface contact with one another, said webs being sealed along their lateral edges and in a multiplicity of longitudinally spaced, transversely extending zones to define a multiplicity of bags therein, each bag being comprised of first and second coextensive panels sealed about a major portion of their common peripheral margin to provide, when said bag articles are separated, an open-ended bag, one of said panels comprising, on the inner face thereof, a fumigant source element having an inner surface and capable of evolving a gaseous agent when said inner surface is exposed, the other of said panels comprising covering means overlying and disengagably held against said inner surface of said element to prevent exposure thereof, displacement of said covering means by separation of said panels, and consequential exposure of said inner surface, enabling evolution and diffusion of said gaseous agent within said bag.

14. The structure of claim 13, wherein said barrier material is a film of synthetic thermoplastic resinous material.

15. The structure of claim 14, wherein said portion of said margin is sealed by fusion of said material.

16. The structure of claim 14, wherein said webs are provided by opposite sides of a unitary, integrally formed tubular structure.

17. The structure of claim 13, wherein said fumigant source element comprises the base layer of a fumigant pad of laminar construction affixed to one of said panels of each said bag, and has a surface remote from said one panel providing said inner surface, said pad including a covering layer affixed to the other of said panels of said bag and providing said covering means.

18. In a method for the containment and treatment of a garment or the like, the steps comprising:

forming an open-ended bag comprising adjacent first and second coextensive panels of gas barrier material sealed about a major portion of their common peripheral margin;

providing a fumigant pad of laminar construction, comprising a base layer including a fumigant source element with a surface, and a covering layer comprising means over-lying and disengagably held against said surface of said fumigant element, said source element being capable of evolving a gaseous agent when said surface thereof is exposed;

inserting said pad into said bag;

affixing said base and covering layers of said pad, respectively, to one and the other of said panels of said bag to provide a bag article, and inserting and item into said bag article, said item causing separation of said panels with consequential exposure of said surface of said fumigant element, thereby activating said pad and enabling evolution and diffusion of said gaseous agent within said bag.

19. In a method for the containment and treatment of a garment or the like, the steps comprising:

forming an open-ended bag comprising adjacent first and second coextensive panels of gas barrier material sealed about a major portion of their common peripheral margin, one of said panels comprising, on the inner face thereof, a fumigant source element having an inner surface and capable of evolving a gaseous agent when said inner surface is exposed, the other of said panels comprising covering means overlying and disengagably held against said inner surface of said source element to prevent exposure thereof; and inserting an item into said bag, said item causing separation of said panels and thereby displacement of said covering means and consequential exposure of said inner surface, enabling evolution and diffusion of said gaseous agent within said bag.

* * * * *